United States Patent
Hong et al.

(10) Patent No.: US 8,529,058 B2
(45) Date of Patent: Sep. 10, 2013

(54) ALTERNATING OPTICAL SYSTEM: MIXING AND MATCHING OPTICS TO MAXIMIZE BINOCULAR VISUAL BENEFITS

(75) Inventors: Xin Hong, Arlington, TX (US); Mutlu Karakelle, Fort Worth, TX (US); Xiaoxiao Zhang, Fort Worth, TX (US); Arthur Bradley, Bloomington, IN (US)

(73) Assignee: Novartis AG, Basel (CH)

( * ) Notice: Subject to any disclaimer, the term of this patent is extended or adjusted under 35 U.S.C. 154(b) by 891 days.

(21) Appl. No.: 12/522,824

(22) PCT Filed: Jan. 11, 2008

(86) PCT No.: PCT/US2008/050881
§ 371 (c)(1),
(2), (4) Date: Jul. 10, 2009

(87) PCT Pub. No.: WO2008/086520
PCT Pub. Date: Jul. 17, 2008

(65) Prior Publication Data
US 2010/0134754 A1    Jun. 3, 2010

Related U.S. Application Data

(60) Provisional application No. 60/884,541, filed on Jan. 11, 2007.

(51) Int. Cl.
G02C 7/02    (2006.01)
G02C 7/04    (2006.01)
G02C 7/06    (2006.01)
A61F 2/16    (2006.01)

(52) U.S. Cl.
USPC ............ 351/159.74; 351/159.08; 351/159.09; 351/159.15; 351/159.55; 351/159.77; 623/6.24; 623/6.25; 623/6.27; 623/6.31

(58) Field of Classification Search
USPC ............. 351/159.08, 159.09, 159.15, 159.55, 351/159.74, 159.77; 623/6.24, 6.25, 6.27, 623/6.31
See application file for complete search history.

(56) References Cited

U.S. PATENT DOCUMENTS

| 5,699,142 A | 12/1997 | Lee et al. | |
| 6,547,822 B1 * | 4/2003 | Lang | 623/6.28 |
| 6,576,012 B2 * | 6/2003 | Lang | 623/6.28 |

(Continued)

FOREIGN PATENT DOCUMENTS

| CA | 2590085 | 6/2006 |
| EP | 0803076 | 10/1997 |

(Continued)

OTHER PUBLICATIONS

International Search Report for PCT/US2008/050881, Publication No. WO2008086520, 4 pages, Jun. 2008.

(Continued)

Primary Examiner — Scott J Sugarman
(74) Attorney, Agent, or Firm — Jonathan E. Prejean (57) ABSTRACT

In one aspect, the present invention provides a method for correcting vision that employs two lenses, at least one of which is a multifocal lens, with different focusing characteristics for use in the two eyes of the patient. The visual performance of each lens (e.g., visual contrast or acuity) is selected in accordance with a predefined relation so as to optimize the binocular visual performance provided by the combination of the lenses.

45 Claims, 5 Drawing Sheets

(56) References Cited

U.S. PATENT DOCUMENTS

| | | |
|---|---|---|
| 7,350,916 B2 | 4/2008 | Hong et al. |
| 7,441,894 B2 | 10/2008 | Zhang et al. |
| 2003/0125806 A1 | 7/2003 | Lang |
| 2006/0116764 A1* | 6/2006 | Simpson .................. 623/6.23 |
| 2007/0182917 A1 | 8/2007 | Zhang et al. |

FOREIGN PATENT DOCUMENTS

| | | |
|---|---|---|
| FR | 2866550 | 8/2005 |
| FR | 2866551 | 8/2005 |
| JP | 2003-177076 | 9/2001 |
| SU | 1124966 | 11/1984 |
| WO | WO 96/21878 | 7/1996 |
| WO | WO 01/84216 | 11/2001 |
| WO | WO 02/34126 | 5/2002 |
| WO | WO 2004/018988 | 3/2004 |
| WO | WO 2006/060480 | 6/2006 |

OTHER PUBLICATIONS

Neison-Quigg et al.; Predicting Binocular Visual Field Sensitivity from Monocular Visual Field Results; Investigative Ophthalmology & Visual Science, vol. 41, No. 8, pp. 2212-2221, Jul. 2000.

* cited by examiner

ALTERNATING OPTICAL SYSTEM: MIXING AND MATCHING OPTICS TO MAXIMIZE BINOCULAR VISUAL BENEFITS

RELATED APPLICATIONS

This application claims priority to PCT Application Serial No. US/2008/050881, filed on Jan. 11, 2008, which claims priority to U.S. provisional application Ser. No. 60/884,541, filed on Jan. 11, 2007.

BACKGROUND

The present invention relates generally to methods and ophthalmic lenses for correcting vision, and more particularly to such methods that provide enhanced binocular vision.

Ophthalmic lenses, such as intraocular lenses (IOLs), are utilized routinely for correcting vision. For example, an IOL can be implanted in a patient's eye to replace, or in some cases augment, the patient's natural crystalline lens. Typically, such an IOL is selected without regard to the visual performance of the other eye of the patient, which might retain its crystalline lens or have another IOL. As many patients enjoy binocular vision, such disregard in selection of the IOL can result in less than optimal binocular vision for the patient.

Accordingly, there is a need for enhanced methods for correcting a patient's vision. In particular there is a need for such methods, and associated ophthalmic lenses, that would provide the patient with improved binocular vision because the vast majority of patients are indeed binocular.

SUMMARY

The present invention relates generally to ophthalmic lenses and methods for enhancing a patient's functional image via binocular summation. In one aspect, the method determines the visual performance of two ophthalmic lenses, at least one of which is a multifocal lens, such that the combined lenses would provide a desired binocular visual performance. In many embodiments, the visual performance can be characterized by image contrast, visual contrast sensitivity and/or visual acuity—though any other suitable measure of visual performance can also be employed.

In one aspect, a method of correcting vision is disclosed that includes providing a lens for enhancing vision in one eye of a patient, and providing another lens for enhancing vision in the other eye of the patient, where the lenses exhibit different focusing characteristics and where at least one of the lenses is selected to be a multifocal lens. Further, the binocular visual performance is related to visual performances of the lenses in accordance with the following relation:

$$B = (L^{kl} + R^{kr})^{\frac{1}{kb}}$$

wherein,
B denotes the binocular visual performance,
L denotes the visual performance of one of the lenses,
R denotes the visual performance of the other lens, and
kl is a parameter having a value no less than 1.0, preferably in a range of about 1.4 to about 4.
kr is a parameter having a value no less than 1.0, preferably in a range of about 1.4 to about 4.
kb is a parameter having a value no less than 1.0, preferably in a range of about 1.4 to about 4.

In a related aspect, the visual performance of each lens can be characterized, e.g., by image contrast and/or visual acuity. For example, the binocular image contrast can be in a range of about 10% to about 80% at a spatial frequency of about 15 cycles/degree, or it can be in a range of about 5% to about 60% at a spatial frequency of about 30 cycles/degree. When utilizing visual acuity as a measure of the visual performance, the binocular visual acuity can be greater than about 20/40, e.g., in a range of about 20/40 to about 20/10.

In some embodiments, the kl, kr and kb parameters can be selected to be in a range of about 2.6 to about 4.5, and preferably about 4, for high-contrast binocular visual acuity performance, where the objects or stimuli to be observed have a contrast higher than about 75%. Further, these kl, kr and kb parameters can be selected to be in a range of about 1 to about 1.6, and preferably about 1.4, for low-contrast binocular visual acuity performance, where the objects or stimuli to be observed have a contrast lower than about 25%. Moreover, these parameters can be selected to be in a range of about 1.7 to about 2.5, and preferably about 2, for binocular contrast sensitivity performance.

In some cases, the binocular visual performance can be characterized by stereo acuity, e.g., a stereo acuity better than about 120 arc-second.

When utilizing the visual contrast as a measure of visual performance, a modulation transfer function (MTF) can be employed to characterize the visual contrast. For example, the MTF value at a selected spatial frequency corresponding to at least one focus of a lens can be employed as a measure of that lens's visual performance. As another example, the MTF value can be obtained by integrating a through-focus MTF curve associated with a multifocal lens between, e.g., its near and far foci.

In another aspect, both lenses include multifocal lenses having different near and/or far focusing powers. For example, a difference of the near and/or the far focusing powers of the two lenses can be in a range of about 0.25 Diopters to about 3 Diopters. In some cases, one of the lenses includes a multifocal lens and the other a monofocal lens, e.g., one having a focusing power intermediate of the near and far foci of the multifocal lens.

In another aspect, the multifocal lens can provide a far focusing power in a range of about −20 D to about 50 D and an add power in a range of about 1 D to about 8 D, e.g., in a range of about 1 D to about 4 D.

In a related aspect, in the above method, the lenses are selected so as to provide the patient with a stereo acuity better than about 120 arc seconds for far and/or near vision.

In another aspect, a method of correcting vision is disclosed that includes implanting a multifocal IOL having a high add power (e.g., an add power equal to or greater than about 3.5 D, e.g., in a range of about 3.5 D to about 8 D) in one eye of a patient, and implanting another multifocal IOL having a lower add power (e.g., an add power equal to or less than about 3.5 D, e.g., in a range of about 0.25 D to about 3.5D) in the other eye of that patient so as to provide an increased near depth-of-focus.

In another aspect, in a method for correcting vision, a distance dominant multifocal IOL can be implanted in one eye of a patient and a regular or a near dominant multifocal IOL can be implanted in the patient's other eye so as to provide improved distance as well as near vision contrast.

In another aspect, the invention provides a method for correcting vision that includes implanting a distance dominant IOL in one eye of a patient and implanting another distance dominant IOL that is slightly myopic (e.g., in a range of about −0.5 to about −2 D) in the other eye of the patient, that is, another distance dominant IOL having a far-focus optical power that is greater than a power needed to image a distant object on the retina. Such combination of IOLs can provide the patient with an improved depth-of-focus for distance vision.

In another aspect, a method for correcting vision is disclosed that includes implanting a monofocal IOL in one eye of a patient and implanting a multifocal IOL in another eye of that patient. The monofocal IOL can provide an optical power for distance vision, e.g., a power in a range of about −20 D to about 50 D, while the multifocal IOL can provide a distance optical power, e.g., one in a range of about −20 D to about 50 D, as well as a near optical power, e.g., one characterized by an add power in a range of about 0.25 D to about 8 D. Such a combination of different IOLs implanted in the two eyes of a patient can provide improved contrast for distance vision.

In another aspect, in a method for correcting vision, a monofocal IOL that is slightly myopic, that is, it provides a refractive optical power less than an optimal refractive power, e.g., by a value in a range of about −0.5 D to about −2 D, can be implanted in one eye of a patient and a regular multifocal IOL can be implanted in the patient's other eye. By way of example, the multifocal IOL can provide a distance optical power in a range of about −20 D to about 50 D and a near optical power characterized by an add power in a range of about 0.25 D to about 8 D. Such a combination of two IOLs implanted in the eyes of a patient can provide improved depth-of-focus for distance vision.

In another aspect, in a method for correcting vision, a distance dominant IOL having a low add power (e.g. an add power in a range of about 0.25 D to about 3.5 D) can be implanted in one eye of a patient and a regular multifocal IOL can be implanted in the other eye of that patient. Such a combination of IOLs can provide improved contrast and depth-of-focus for distance vision.

In another aspect, a method for correcting vision is disclosed that includes implanting a monofocal IOL that is slightly myopic (e.g., by a value in a range of about −0.5 D to about −2 D less than an optimal refractive power) in one eye of a patient and implanting a distance dominant multifocal IOL in the other eye of that patient. Such combination of IOLs can result in improved contrast and depth-of-focus for distance vision.

In another aspect, the invention provides a lens kit for correcting a patient's vision, which includes a lens (e.g., an IOL) for use in one eye of the patient, and another lens (e.g., another IOL) for use in the other eye of that patient, where the lenses exhibit different focusing characteristics so as to provide the patient with a binocular visual performance in a selected range. At least one of the lenses is a multifocal lens. Further, the binocular visual performance is related to the visual performances of the lenses in accordance with the following relation:

$$B = (L^{kl} + R^{kr})^{\frac{1}{kb}}$$

wherein,

B denotes the binocular visual performance,

L denotes the visual performance of one of the lenses,

R denotes the visual performance of the other lens, and kl is a parameter having a value no less than 1.0, preferably in a range of about 1.4 to about 4.

kr is a parameter having a value no less than 1.0, preferably in a range of about 1.4 to about 4.

kb is a parameter having a value no less than 1.0, preferably in a range of about 1.4 to about 4.

In a related aspect, in the above lens kit, the visual performance is characterized by image contrast or visual acuity. By way of example, in some embodiments, the image contrast of the two lenses are selected such that the binocular image contrast lies in a range of about 10% to about 80% at a spatial frequency of about 15 cycles/degree. In other embodiments, the two lenses are selected such that the binocular visual acuity would lie in a range of about 20/40 to about 20/10.

In other aspects, in the above lens kit, the multifocal lens exhibits a far-focus optical power in a range of about −15 D to about 50 D and an add power in a range of about 1 D to about 4 D. In some cases, the other lens is also a multifocal lens with a different far focus and/or add power. For example, a difference between the far-focus and/or add powers of the lenses can be in a range of about 0.25 D to about 2 D. Alternatively, the other lens can be a monofocal lens, e.g., one with a focusing power in a range of about −15 D to about 50 D. In many embodiments, the focusing power of the monofocal lens is selected to lie between the near and far foci of the multifocal lens.

In another aspect, the lenses in above lens kit can comprise intraocular lenses.

In yet another aspect, the lenses provide the patient with a stereo acuity better than about 120 arc seconds for near and/or far vision.

In other aspects, a method for correcting vision is disclosed that comprises selecting a binocular visual performance (B) for a patient, and selecting a visual performance (L) of a lens (e.g., an IOL) for use in one eye of the patient as a function of a visual performance (R) of another lens (e.g., another IOL) in the other eye of that patient in accordance with the following relation:

$$B = (L^{kl} + R^{kr})^{\frac{1}{kb}}$$

wherein,

B denotes the binocular visual performance,

L denotes the visual performance of one of the lenses,

R denotes the visual performance of the other lens, and kl is a parameter having a value no less than 1.0, preferably in a range of about 1.4 to about 4, kr is a parameter having a value no less than 1.0, preferably in a range of about 1.4 to about 4, kb is a parameter having a value no less than 1.0, preferably in a range of about 1.4 to about 4, and wherein at least one of the first and the second lenses is a multifocal lens.

In a related aspect, the binocular visual performance can be characterized by an image contrast, e.g., in a range of about 10% to about 80% at a spatial frequency of about 15 cycles/degree or in a range of about 5% to about 60% at a spatial frequency of about 30 cycles/degree. In some cases, the binocular visual performance can be characterized by a visual acuity, e.g., in a range of about 20/40 to about 20/10.

Further understanding of various aspects of the invention can be obtained by reference to the following detailed description together with the associated drawings, which are briefly discussed below.

DETAILED DESCRIPTION

The present invention generally provides methods and ophthalmic lenses for enhancing functional vision of a patient over a wide range of distances by utilizing binocular vision. In one aspect, the invention provides a method of correcting a patient's vision by utilizing two lenses having different focusing characteristics, one of which is used in one eye of the patient and another in the other eye. The lenses can be selected so as to collectively provide the patient with a binocular visual performance (e.g., characterized by image contrast or visual acuity) in a selected focus range. In the embodiments that follow, the salient features of the invention are primarily discussed in connection with intraocular lenses (IOLs). The term "intraocular lens" and its abbreviation "IOL" are used herein interchangeably to describe lenses that are implanted into the interior of an eye to either replace the eye's natural lens or to otherwise augment vision regardless of whether or not the natural lens is removed. Intracorneal lenses and phakic lenses are examples of lenses that may be implanted into the eye without removal of the natural lens. It should also be understood that the teachings of the invention are also applicable to other ophthalmic lenses, such as contact lenses.

Figure 1:
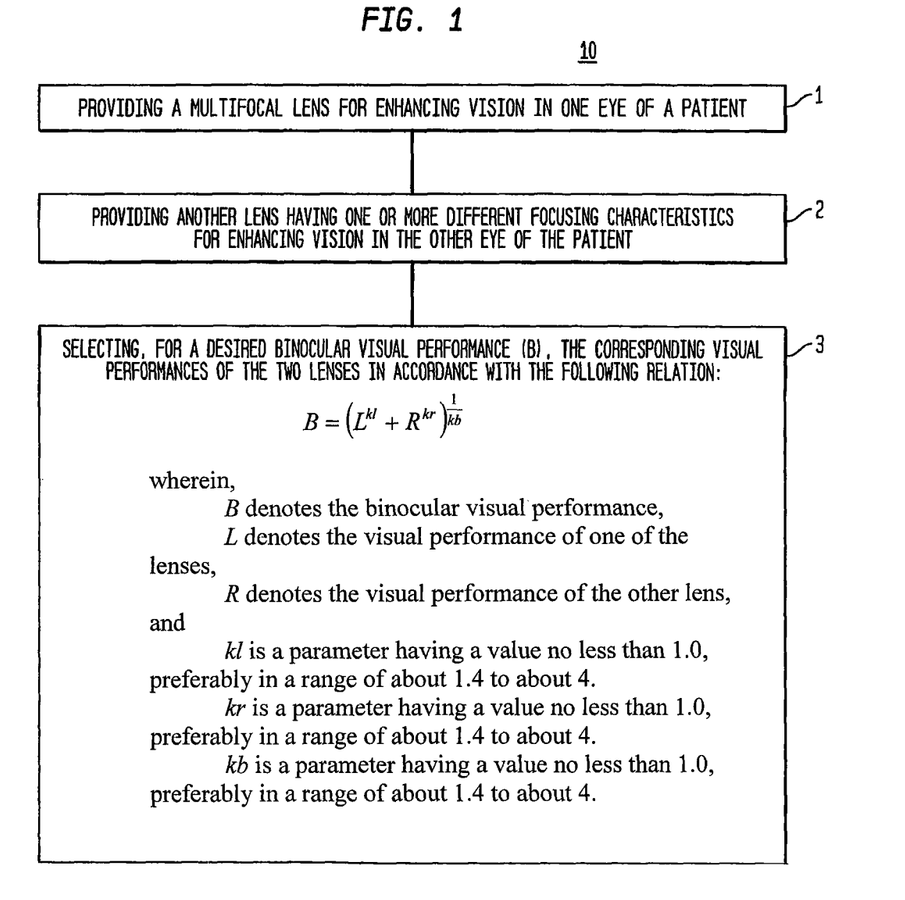
FIG. 1 is a flow chart depicting various steps in an exemplary embodiment of a method according to the teachings of the invention for correcting vision.

With reference to a flow chart 10 shown in FIG. 1, a method of correcting vision in accordance with one embodiment of the invention, an ophthalmic lens is provided for enhancing vision in one eye of a patient (step 1), and another ophthalmic lens having at least one different focusing characteristic is provided for enhancing vision in the other eye of the patient (step 2), wherein at least one of the lenses is a multifocal lens, e.g., one characterized by near and far foci. The term "focusing characteristic," as used herein, can refer to any desirable refractive and/or diffractive parameter of the lens. By way of example, for a monofocal lens, the focusing characteristic can refer to the lens's focusing power. For a multifocal lens, the focusing characteristic can refer to the far focusing power and/or the add power of that lens.

As the two eyes may see images with different optical quality, in many embodiments, one or more of the following factors are typically considered to optimize the patient's function image by using binocular vision: binocular summation and rivalry, binocular visual quality and stereo acuity. A target can be seen if only the right eye or the left eye sees it, or if both eyes see it simultaneously. Thus, the probability that the target is seen when both eyes are looking is (1−p), where p is the probability that neither eye would see the target. For example, if the probability that the right eye or the left eye alone can see the target is 0.6, the probability that neither eye would see that target is (0.4)(0.4)=0.16. Hence, the probability that the target would be seen when both eyes are looking is (1−0.16=0.84). Thus, utilizing both eyes can provide visual enhancement even without considering neural summation.

With continued reference to the flow chart 10 of FIG. 1, in many embodiments, within a desired focus range, for a given desired binocular visual performance (characterized, e.g., by image contrast, contrast sensitivity or visual acuity), the corresponding visual performance of the two lenses are chosen in accordance with the following relation:

$$B = (L^{kl} + R^{kr})^{\frac{1}{kb}} \qquad \text{Eq. (1)}$$

wherein,

B denotes the binocular visual performance,

L denotes the visual performance of one of the lenses,

R denotes the visual performance of the other lens, and kl is a parameter having a value no less than 1.0, preferably in a range of about 1.4 to about 4.

kr is a parameter having a value no less than 1.0, preferably in a range of about 1.4 to about 4.

kb is a parameter having a value no less than 1.0, preferably in a range of about 1.4 to about 4.

In some embodiments, the visual performance can be characterized by image contrast. As known to those having ordinary skill in the art, a quantitative measure of image contrast provided by a lens can be obtained by calculating and/or measuring a modulation transfer function (MTF) associated with that lens. In general, a contrast or modulation associated with an optical signal, e.g., a two-dimensional pattern of light intensity distribution emanated from or reflected by an object to be imaged or associated with the image of such an object, can be defined in accordance with the following relation:

$$\frac{I_{max} - I_{min}}{I_{max} + I_{min}} \qquad \text{Eq. (2)}$$

wherein $I_{max}$ and $I_{min}$ indicate, respectively, a maximum or a minimum intensity associated with the signal. Such a contrast can be calculated or measured for each spatial frequency present in the optical signal. An MTF of an imaging optical system, such as the combined IOL and the cornea, can then be defined as a ratio of a contrast associated with an image of an object formed by the optical system relative to a contrast associated with the object. As is known, the MTF associated with an optical system is not only dependent on the spatial frequencies of the intensity distribution of the light illuminating the system, but it can also be affected by other factors, such as the size of an illumination aperture as well as the wavelength of the illuminating light.

In many embodiments, the MTF can be measured and/or calculated for light having a wavelength of about 550 nm—though other wavelengths or a combination of wavelengths can also be employed—at an aperture size of about 3 mm. By way of example, the MTF values can be obtained via measurements in a model eye or via calculations by ray tracing, e.g., by employing a raytracing software, such as OSLO premium raytracing program, marketed by Lambda Research Corporation of Littleton, Mass., U.S.A.

In some embodiments in which the visual performance is characterized by MTF, the binocular visual performance can be described in terms of the in-focus MTF value at a given spatial frequency (e.g., at 15 or 30 cycles/degree) corresponding to a focal plane (e.g., near, intermediate or far foci). Given a binocular MTF value, the respective MTF values of the two lenses corresponding to that focal plane are determined so as to satisfy the above Equation (1). In some cases, the MTF can be integrated over a spatial frequency range (e.g., from 15 to 30 cycles/degree) as a measure of image contrast at a focal plane. In other cases, a through-focus MTF (either of a given spatial frequency, or of a integrated spatial frequency range as mentioned above) curve plotted over a selected defocus range, e.g., from the near focus to the far focus, to obtain a measure of the visual contrast.

Figure 2:
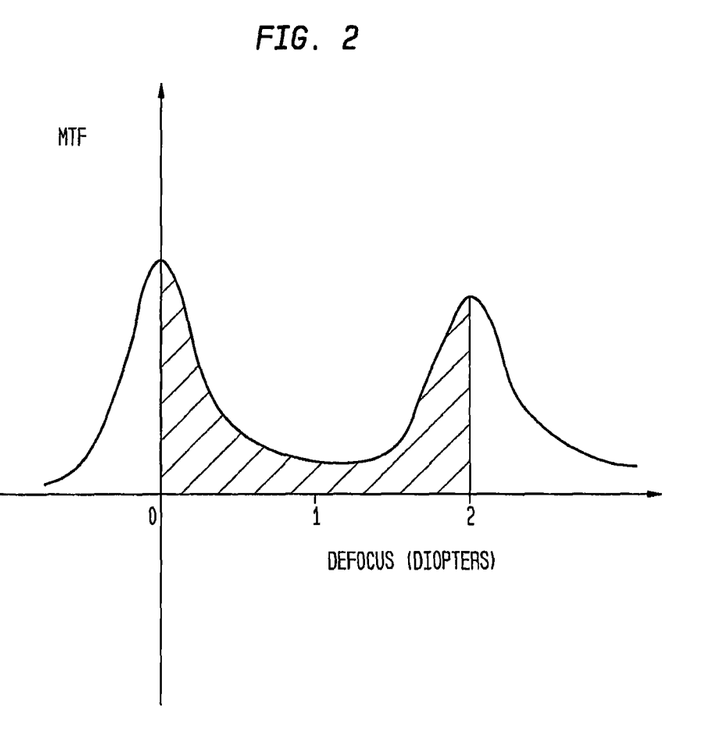
FIG. 2 is a hypothetical modulation transfer function (MTF) associated with a multifocal ophthalmic lens, FIG. 3 schematically depicts an exemplary multifocal ophthalmic lens suitable for use in some embodiments of the invention, FIG. 4 schematically shows an exemplary monofocal ophthalmic lens suitable for use in some embodiments of the invention, FIG. 5 schematically depicts a lens kit according to one embodiment of the invention providing two lenses with different focusing characteristics for use in two eyes of a patient.

By way of example, FIG. 2 schematically depicts a hypothetical through-focus MTF curve (e.g. for a light wavelength of about 550 nm) at a given spatial frequency (e.g., 15 cycles/degree) associated with a multifocal lens providing a near and a far focus. In some cases, a measure of the visual performance of such a hypothetical lens can be obtained by calculating the area under the curve (i.e. by integrating the MTF as a function of spatial frequency) over a selected defocus extent (e.g., from the near focus to the far focus as shown by the cross-hatched area). Alternatively, an average of the MTF values corresponding to the near and far foci can be utilized. By way of further examples, in the case of a monofocal lens, the MTF value at the lens's focus can provide a measure of its visual performance. Alternatively, the area under the MTF peak surrounding the lens's focus can be utilized.

By way of example, in some embodiments, the image contrast of the two ophthalmic lenses are selected such that the binocular visual contrast would lie in a range of about 10% to about 80% at a spatial frequency of about 15 cycles/degree, or in a range of about 5% to about 60% at a spatial frequency of about 30 cycles/degree.

Other measures of visual performance can also be employed to obtain an optimal combination of two lenses for use in the two eyes of a patient. One such measure comprises the visual acuity, which can be determined by a variety of methods. For example, in some cases, letter acuity eye charts can be employed for this purpose. In other cases, the optical resolving power of a lens can be determined (measured or calculated) in a model eye as a measure of visual acuity provided by that lens. In some embodiments, the visual acuity associated with the two lenses are selected so as to obtain a binocular visual acuity in a range of, e.g., about 20/40 to about 20/10.

In some embodiments, the kl, kr and kb values are selected to be in a range of about 2.6 to about 4.5, and preferably about 4, when the binocular visual performance is characterized by a high contrast visual acuity performance (e.g., to enhance binocular visual acuity by about 10% or more for stimuli of high-contrast (i.e. contrast higher than about 75%)), and these kl, kr and kb values are selected to be in a range 1 to about 1.6, and preferably about 1.4, when the binocular visual performance is characterized by a binocular low contrast visual acuity performance (e.g., to enhance binocular visual acuity up to about 60% for stimuli of low-contrast (i.e. contrast lower than about 25%)). Further, in some cases, these values can be selected to be in a range of about 1.7 to about 2.5, and preferably about 2, when the binocular visual performance is characterized by a binocular contrast sensitivity performance (e.g., to enhance binocular visual contrast sensitivity up to about 40%).

Figure 3:
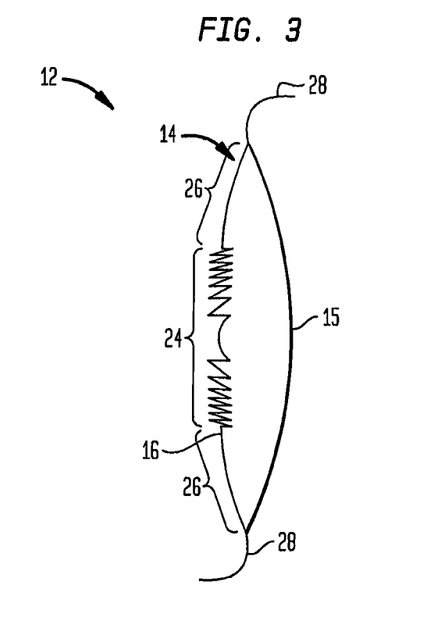

In some embodiments, the two lenses are multifocal lenses exhibiting different far-focus and/or add powers. By way of example, in some cases, the two multifocal lenses exhibit a difference in their far-focus and/or add powers in a range of about 0.25 D to about 3 D, e.g., in a range of about 0.25 D to about 2 D. FIG. 3 schematically shows an example of such a multifocal IOL 12 having an optic 14, which comprises an anterior surface 16 and a posterior surface 18, that provides a far-focus power, e.g., in a range of about −20 D to about 50 D (and preferably in a range of about −5 D to about 34 D). A diffractive structure 24 disposed on the anterior surface 20 provides the IOL with an add power, e.g., in a range of about 1 D to about 4 D (preferably, in a range of about 2 D to about 3 D). In this embodiment, the diffractive structure is truncated, that is, it is surrounded by a portion 26 of the anterior surface that lacks diffractive structures. In some embodiments, the diffractive structure is characterized by a plurality of diffractive zones separated from one another by a plurality of steps that exhibit a decreasing height as a function of increasing distance from the optical axis. The lens 12 further includes a plurality of fixation members (haptics) 28 that facilitate its placement in the eye. Further details regarding some examples of multifocal ophthalmic lenses suitable for use in the practice of the invention can be found in U.S. Pat. No. 5,699,142, and a pending U.S. patent application Ser. No. 11/000,770 entitled "Apodized Aspheric Diffractive Lenses," both of which are herein incorporated by reference.

A multifocal lens can exhibit static optical corrections for distance, near and/or intermediate objects. The depth of focus corresponding to each correction can, however, extend only to a certain value (e.g., about 0.75 D) for reasonable visual function. Thus, a static pseudo-accommodation provided by the lens can leave notches of visual deficits in optical through-focus visual performance. The locations of such deficit notches are typically determined by the lens parameters, such as the add power, targeted refraction, distance/near energy balance, and aberrations. In many embodiments of the invention, the add power and/or the targeted refraction of the two different lenses, each intended for one of the eyes of the patient, are selected such that their deficit notches appear at different locations in the two eyes, thus substantially disappearing when summed binocularly. In other words, the two lenses cooperatively provide the patient with an enhanced binocular vision.

In some embodiments, one or more parameters of a multifocal lens can be adjusted so as to obtain a desired visual performance for that lens. For example, with reference to FIG. 3, a certain degree of asphericity (e.g., one characterized by a conic constant in a range of about −11.1 (minus 11.1) to about −1030 (minus 1030) can be imparted to at least one of the anterior or posterior optical surfaces so as to minimize spherical aberration and hence improve MTF, especially for large aperture sizes. Also, the step heights of the diffractive steps of a diffractive structure disposed on at least one of the lens surfaces can be adjusted to achieve the desired light energy distribution to the foci of interests. By way of example, the step height at each zone boundary can be defined in accordance with the following relation:

$$\text{Step height} = \frac{\lambda}{a(n_2 - n_1)} f_{apodize} \qquad \text{Eq. (3)}$$

wherein
  λ denotes a design wavelength (e.g., 550 nm),
  a denotes a parameter that can be adjusted to control diffraction efficiency associated with various orders, e.g., a can be selected to be 2.5;
  $n_2$ denotes the index of refraction of the optic,
  $n_1$ denotes the refractive index of a medium in which the lens is placed, and
  $f_{apodize}$ represents a scaling function whose value decreases as a function of increasing radial distance from the intersection of the optical axis with the anterior surface of the lens. By way of example, the scaling function $f_{apodize}$ can be defined by the following relation:

$$f_{apodize} = 1 - \left(\frac{r_i}{r_{out}}\right)^3 \quad \text{Eq. (4)}$$

wherein
  $r_i$ denotes the radial distance of the $i^{th}$ zone,
  $r_{out}$ denotes the outer radius of the last bifocal diffractive zone. Other apodization scaling functions can also be employed, such as those disclosed in the afore-mentioned patent application entitled "Apodized Aspheric Diffractive Lenses."

In addition, the diameters of the diffractive zones (the locations of the zone boundaries) can be adjusted to achieve desired focal length or add power. In some of such embodiments, the radial location of a zone boundary ($r_i$) is selected in accordance with the following relation:

$$r_i^2 = (2i+1)\lambda f \quad \text{Eq. (5)}$$

wherein
  i denotes the zone number (i=0 denotes the central zone),
  $r_i$ denotes the radial location of the $i^{th}$ zone,
  λ denotes the design wavelength, and
  f denotes the focal length for an add power.

Further, the depth-of-focus at the near and/or far focus can be adjusted by selectively varying the areas of a plurality of annular diffraction zones. By way of example, the radial location of a zone boundary can be determined in accordance with the following relation:

$$r_i^2 = (2i+1)\lambda f + g(i) \quad \text{Eq. (6).}$$

wherein
  i denotes the zone number (i=0 denotes the central zone),
  λ denotes the design wavelength,
  f denotes a focal length of the near focus, and
  g(i) denotes a non-constant function.

In some cases, the function g(i) is defined in accordance with the following relation:

$$g(i) = (ai^2 + bi)f \quad \text{Eq. (7),}$$

wherein
  i denotes the zone number,
  a and b are two adjustable parameters, and
  f denotes the focal length of the near focus. By way of example, a can be in a range of about 0.1λ to about 0.3λ, and b can be in a range of about 1.5λ to about 2.5λ, where λ denotes the design wavelength. By adjusting the function g(i), the depth-of-focus associated with the near and/or far focus can be varied. For example, the through-focus visual contrast curve associated with those foci can be broadened, which can result in diverting some of the incident light to an intermediate focal region.

Further details regarding multifocal lenses suitable for use in the practice of the invention can be found in co-pending U.S. Patent Application entitled "Pseudo-Accommodative IOL Having Diffractive Zones With Varying Areas" having a Ser. No. 11/350,437, filed on Feb. 9, 2006; and in co-pending U.S. Patent Application entitled "Pseudo-Accommodative IOL Having Multiple Diffractive Patterns" having a Ser. No. 11/350,497, and filed on Feb. 9, 2006. Both of these applications are herein incorporated by reference.

Figure 4:
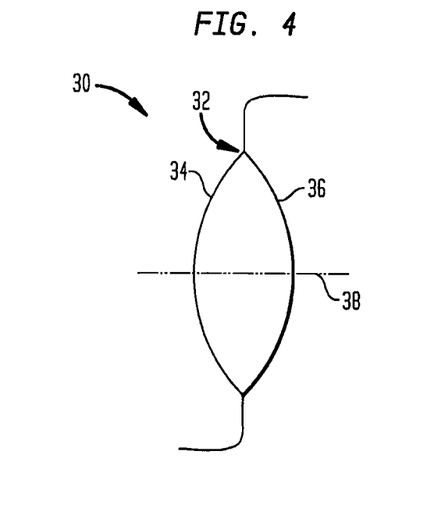

In some other embodiments, while one of the lenses is a multifocal lens, the other is a monofocal lens. By way of example, the multifocal lens can provide a far-focus and a near-focus power. Further, in many embodiments, the monofocal lens can provide a focus intermediate of the far and near foci of the multifocal lens. A variety of monofocal ophthalmic lenses (e.g., monofocal IOLs) can be employed. By way of example, FIG. 4 schematically depicts such a monofocal ophthalmic lens 30 having an optic 32 comprising an anterior optical surface 34 and a posterior optical surface 36 disposed about an optical axis 38. In some cases, at least one of the optical surfaces can exhibit a degree of asphericity, e.g., so as to alleviate spherical aberrations. In some embodiments, the surface asphericity can be adjusted so as to obtain a desired visual performance of the lens. Some exemplary monofocal lenses suitable for use in the practice of the invention are disclosed in U.S. patent application Ser. No. 11/397,332 entitled "Intraocular Lens," which is herein incorporated by reference.

In some embodiments, the above Equation (1) can be utilized to determine, for a desired binocular visual performance, the visual performance of one ophthalmic lens for use in one eye of a patient based on the measured (or calculated) visual performance of another lens in the other eye of that patient. For example, in many cases, an IOL is implanted in only one eye of the patient with the other eye retaining its natural crystalline lens. In such a case, the visual performance of the natural lens can be measured (e.g., in terms of visual acuity) and the above Equation (1) can be employed to determine the requisite visual performance of the IOL for implantation in the other eye so as to provide the patient with a desired binocular visual performance.

Figure 5:
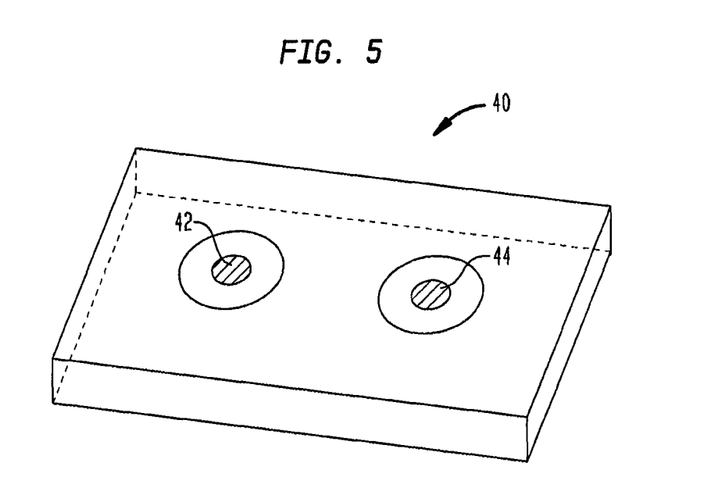

In some aspects, the invention provides a lens kit having two ophthalmic lenses (e.g., IOLs), each of which is intended for use in one eye of a patient, selected in accordance with the above teachings, wherein at least one of the lenses is a multifocal lens. For example, FIG. 5 schematically shows such a lens kit 40 that is composed of intraocular lenses 42 and 44 (e.g., two multifocal lenses, or a multifocal and a monofocal lens). Each lens provides a requisite refractive correction for the eye for which it is intended. In addition, the visual performances of the lenses (e.g., as characterized by visual contrast or acuity) can be selected, e.g., in accordance with the above Equation (1), such that the binocular visual performance provided by the combination of the lenses would be at a desired value.

Figure 6:
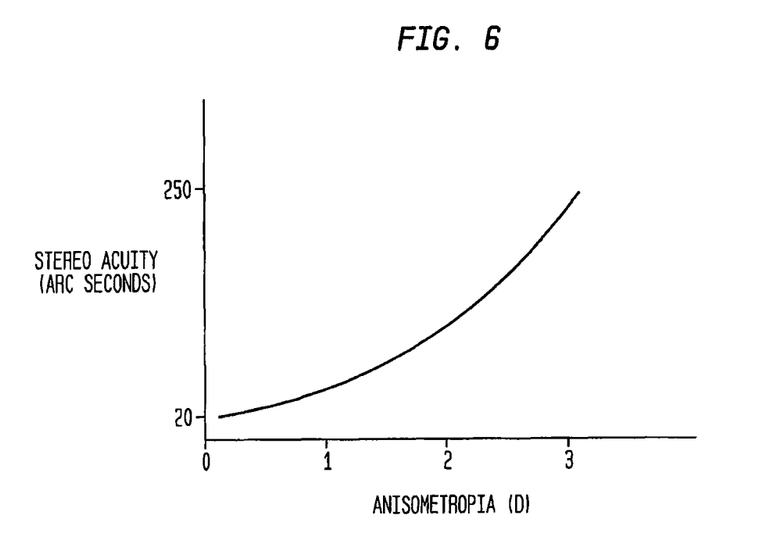
FIG. 6 shows a hypothetical exemplary relationship between stereo acuity and anisometropia.

In many embodiments, the lenses for use in the two eyes of a patient (e.g., two IOLs for implantation in the two eyes) are selected such that the binocular stereo acuity for near and/or far vision is preferably better than about 120 arc seconds. The near vision can correspond, e.g., to viewing distances less than about 45 cm from the eye and far vision can correspond, e.g., to viewing distances greater than about 80 cm from the eye. As known in the art, stereopsis refers to depth perception from binocular vision. By way of example, the stereo acuity can be computed with the assistance of measured stereoacuity-anisometropia relationship, such as a hypothetical relationship shown in FIG. 6. The different multifocal optics in different eyes of a patient can provide different amounts of anisometropia (the difference between refractive powers between eyes) for either distance, near or intermediate vision. The stereo acuity can be quickly assessed from known anisometropia.

The above teachings of the invention can be implemented in a variety of ways with different combinations of IOLs for implantation in the eyes of patients so as to achieve a desired binocular visual performance, e.g., as characterized by image contrast, stereo acuity, or any other metric of visual performance. In the above embodiments, such IOLs were described primarily in terms of their visual performance. In the following, some exemplary combinations of IOLs for implantation in the two eyes of a patient are discussed in terms of the optometric parameters of the lenses.

By way of example, in some cases, a multifocal IOL having a high add power (e.g., an add power equal or greater than about 3.5 D, e.g., in a range of about 3.5 D to about 8 D) can be implanted in one eye of a patient, and implanting another multifocal IOL having a lower add power (e.g., an add power equal to or less than about 3.5 D, e.g., in a range of about 0.25 D to about 3.5 D) can be implanted in the other eye of that patient so as to provide an increased depth-of-focus for near vision.

In another case, a distance dominant multifocal IOL can be implanted in one eye of a patient and a regular or a near dominant multifocal IOL can be implanted in the patient's other eye so as to provide improved distance as well as near vision contrast. A distance dominant multifocal IOL, as used herein, refers to a multifocal IOL that distributes a larger fraction of the light energy to its far focus rather than its near focus, e.g., it causes more than about 50%, and in some cases more than about 60%, or more than about 70%, or more than about 80%, of the light energy incident thereon from a distant object (e.g., an object at a distance greater than about 2 m from the eye) to its far focus, e.g., at an aperture (pupil) size of about 3.5 mm. In contrast, a regular IOL, as used herein, refers to an IOL that distributes the light received from a distant object roughly equally between its near and far foci (e.g., 40% of the light would be transmitted to the far focus and 40% to the near focus), e.g., at an aperture size (pupil size) of about 3.5 mm. Further, a near dominant IOL, as used herein, refers to an IOL that transmits a larger fraction of light energy received from a distant object to its near focus (e.g., more than about 50% of the light energy, or more than about 60%, or more than about 70%, or more than about 80%), e.g., at an aperture size (pupil size) of about 3.5 mm.

By way of another example, in some cases, a distance dominant multifocal IOL can be implanted in one eye of a patient and another distance dominant IOL that is slightly myopic (e.g., in a range of about −0.5 to about −2 D) at its far focus can be implanted in the other eye of the patient. A slightly myopic multifocal IOL provides a distance optical power that is greater than (e.g., by about 0.5 to about 2 D) than what is optimally needed to form an image of a distant object on the patient's retina. Such combination of IOLs can provide the patient with an improved depth-of-focus for distance vision.

In another case, a monofocal IOL is implanted in one eye of a patient and a multifocal IOL is implanted in the patient's other eye. The monofocal IOL can provide an optical power for distance vision, e.g., a power in a range of about −20 D to about 50 D, while the multifocal IOL can provide a distance optical power, e.g., one in a range of about −20 D to about 50 D, as well as a near optical power, e.g., one characterized by an add power in a range of about 0.25 D to about 8 D. Such a combination of different IOLs implanted in the two eyes of a patient can provide improved contrast for distant vision.

By way of another example, in another case, a monofocal IOL that is slightly myopic (e.g., by a value in a range of about −0.5 D to about −2 D)—that is, a monofocal IOL that provides an optical power greater than what is optimally needed to image a distant object onto the retina—can be implanted in one eye of a patient and a regular multifocal IOL can be implanted in the patient's other eye. By way of example, the multifocal IOL can provide a distant optical power in a range of about −20 D to about 50 D and a near optical power characterized by an add power in a range of about 0.25 D to about 8 D. Such a combination of two IOLs implanted in the eyes of a patient can provide improved depth-of-focus for distance vision.

In another embodiment, a distance dominant IOL having a low add power (e.g. an add power equal to or less than about 3.5 D, e.g., in a range of about 0.25 D to about 3.5 D) can be implanted in one eye of a patient and a regular multifocal IOL can be implanted in the other eye of that patient. Such a combination of IOLs can provide improved contrast and depth-of-focus for distance vision.

In another embodiment, a monofocal IOL that is slightly myopic (e.g., by a value in a range of about −0.5 D to about −2 D) can be implanted in one eye of a patient and a distance dominant multifocal IOL can be implanted in the other eye of that patient. Such a combination of IOLs can result in improved contrast and depth-of-focus for distance vision.

Table 1 below summarizes the various combinations of IOLs discussed in the above few paragraphs, and some of their associated advantages:

TABLE 1

| 1st Eye | 2nd Eye | Exemplary Binocular Vision Performance Attribute |
|---|---|---|
| High power multifocal IOL | Lower add power multifocal IOL | Increased depth-of-focus for near vision |
| Distance dominant multifocal IOL | Regular or near dominant multifocal IOL | Improved contrast for distant and near vision |
| Distance dominant multifocal IOL | Distant dominant multifocal IOL that is slightly myopic (e.g., by a value in a range of about −0.5 to about −2 D) | Improved depth-of-focus for distant vision |
| Monofocal IOL | Regular multifocal IOL | Improved contrast for distant vision |
| Monofocal IOL that is slightly myopic (e.g., by a value in a range of about −0.5 to about −2 D) | Regular multifocal IOL | Improved depth-of-focus for distant vision |

TABLE 1-continued

| 1st Eye | 2nd Eye | Exemplary Binocular Vision Performance Attribute |
|---|---|---|
| Low add power and distance dominant multifocal IOL | Regular multifocal IOL | Improved contrast and depth-of-focus for distant vision |
| Monofocal IOL that is slightly myopic (e.g., by a value in a range of about −0.5 to about −2 D) | Distant dominant multifocal IOL | Improved contrast and depth-of-focus for distant vision |

To further illustrate some salient features of the invention, the following hypothetical examples are provided. It should be understood that these examples are provided only for illustrative purposes and are not intended to necessarily indicate the optimal binocular visual performance attainable by practicing the teachings of the invention.

DESIGN EXAMPLE 1

Figure 7A:
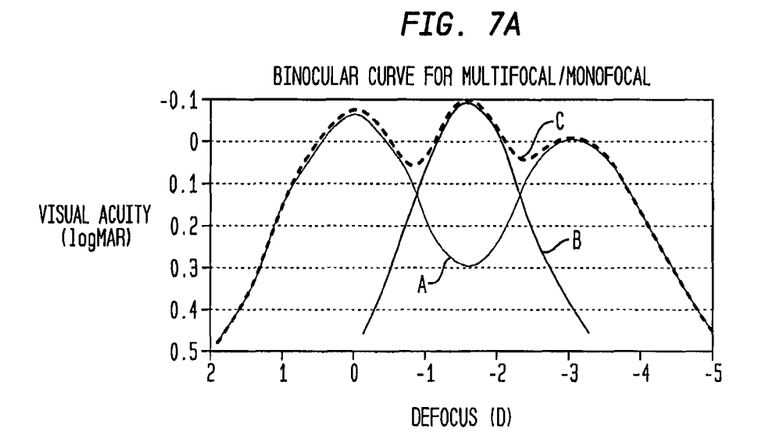
FIG. 7A depicts hypotherical visual acuity curves for a multifocal lens, a monofocal lens, and a resultant binocular visual acuity curve achieved by utilizing the two lenses in two eyes of a patient.

A multifocal lens characterized by a targeted refraction of 0 D and an add power of +3.0 D is provided for use in one eye of a patient. FIG. 7A shows a calculated through-focus visual acuity curve A (visual acuity as a function of defocus) associated with this lens. The visual acuity is represented by logarithm of minimum angle of resolution (MAR in units of armin). A monofocal lens having a targeted refraction of −1.5 D is provided for the other eye of the patient. This lens is assumed to exhibit a degree of asphericity (i.e. a conic constant of −42) in one of its surface to reduce spherical aberration effects. A calculated through-focus visual acuity associated with this monofocal lens is also presented in FIG. 7A as curve B. A predicted binocular visual performance, as characterized by a binocular through-focus visual acuity curve, was calculated by utilizing the above Equation (1) with the parameter kl, kr and kb set to 4. This binocular visual acuity curve (shown by dashed lines as curve C) shows that the combination of the lenses provides a visual acuity better than about 20/25 from infinity to a distance of about 30 cm.

DESIGN EXAMPLE 2

Figure 7B:
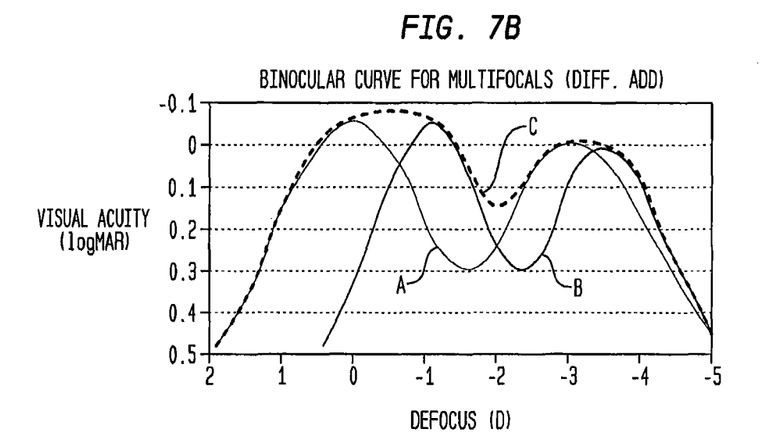
FIG. 7B depicts hypothetical visual acuity curves for two multifocal lenses with different focusing characteristics, and a resultant visual acuity curve achieved by utilizing those lenses in the two eyes of a patient.

A multifocal lens characterized by a targeted refraction of 0 D and an add power of +3.0 D is provided for use in one eye of a patient. FIG. 7B shows a calculated through-focus visual acuity curve A (visual acuity as a function of defocus) associated with this lens. Another multifocal lens having a targeted refraction of 1 D and an add power of 2.5 D is provided for the other eye of the patient. A calculated through-focus visual acuity curve associated with this other multifocal lens is also presented in FIG. 7B (curve B). A predicted binocular visual performance, as characterized by a binocular through-focus visual acuity curve, was calculated by utilizing the above Equation (1) with the parameter kl, kr and kb set to 4. This binocular visual acuity (curve C shown by dashed lines) illustrates that the combined lenses provide a visual acuity better than about 20/30 from infinity to a distance of about 30 cm.

Those having ordinary skill in the art will appreciate that various modifications can be made to the above embodiments without departing from the scope of the invention.

What is claimed is:

1. A method of correcting vision, comprising the steps of:
a) providing a first lens for enhancing vision in one eye of a patient, and
b) providing a second lens for enhancing vision in the other eye of the patient,
wherein at least one of the first or the second lenses is a multifocal lens, and the first and the second lenses exhibit different focusing characteristics so as to provide the patient with a binocular visual performance in a selected range, the binocular visual performance being related to a visual performance of the first lens and the second lens in accordance with the following relation:

$$B = (L^{kl} + R^{kr})^{\frac{1}{kb}}$$

wherein,
B denotes the binocular visual performance,
L denotes the visual performance of one of the lenses,
R denotes the visual performance of the other lens, and
kl is a parameter having a value no less than 1.0, preferably in a range of about 1.4 to about 4,
kr is a parameter having a value no less than 1.0, preferably in a range of about 1.4 to about 4,
kb is a parameter having a value no less than 1.0, preferably in a range of about 1.4 to about 4, and
wherein each of the visual performances of the first lens and the second lens is characterized by image contrast.

2. The method of claim 1, wherein kl, kr and kb are equal to each other.

3. The method of claim 1, further comprising selecting kr to be in a range of about 2.6 to about 4.5 to provide high-contrast binocular visual acuity performance.

4. The method of claim 3, further comprising selecting parameter kl to be in a range of about 2.6 to about 4.5, and parameter kb to be in a range of about 2.6 to about 4.5.

5. The method of claim 1, further comprising selecting kr to be about 4.

6. The method of claim 5, further comprising selecting parameter kl to be about 4 and selecting parameter kb to be about 4.

7. The method of claim 1, further comprising selecting kr to be in a range of about 1 to about 1.6 to provide low-contrast binocular visual acuity performance.

8. The method of claim 7, further comprising selecting parameter kl to be in a range of about 1 to about 1.6, and parameter kb to be in a range of about 1 to about 1.6.

9. The method of claim 1, further comprising selecting kr to be in a range of about 1.7 to about 2.5 to provide binocular visual contrast sensitivity performance.

10. The method of claim 9, further comprising selecting parameter kl to be in a range of about 1.7 to about 2.5, and parameter kb to be in a range of about 1.7 to about 2.5.

11. The method of claim 1, wherein the image contrast is characterized by a modulation transfer function (MTF).

12. The method of claim 11, wherein the MTF characterizations associated with each of the first and the second lenses comprises a MTF value at a selected spatial frequency corresponding to at least one focus of the first or the second lens, respectively.

13. The method of claim 11, wherein the MTF associated with each of the first and the second lenses comprises an integrated MTF value over a range of spatial frequency corresponding to at least one focus of the first or the second lens, respectively.

14. The method of claim 11, wherein the MTF characterization associated with the multifocal lens comprises a through-focus MTF plotted over a defocus range extending from a near focus to a far focus of the multifocal lens.

15. The method of claim 1, wherein each of the visual performances of the first lens and the second lens is characterized by visual acuity.

16. The method of claim 15, wherein the visual acuity is selected to be greater than about 20/40.

17. The method of claim 1, further comprising selecting both the first and the second lenses to be multifocal lenses.

18. The method of claim 17, further comprising selecting the multifocal lenses to have different add powers.

19. The method of claim 17, further comprising selecting a difference between the add powers of the first and the second lenses to be in a range of about 0.25 Diopters to about 3 Diopters.

20. The method of claim 17, further comprising selecting the first and the second lenses to have different far focusing powers.

21. The method of claim 20, further comprising selecting a difference between the far focusing powers of the first and the second lenses to be in a range of about 0.25 Diopters to about 3 Diopters.

22. The method of claim 1, wherein the first and the second lenses comprise intraocular lenses (IOLs).

23. A method of correcting vision, comprising the steps of:
a) providing a first lens for enhancing vision in one eye of a patient, and
b) providing a second lens for enhancing vision in the other eye of the patient, wherein at least one of the first or the second lenses is a multifocal lens, and the first and the second lenses exhibit different focusing characteristics so as to provide the patient with a binocular visual performance in a selected range, the binocular visual performance being related to a visual performance of the first lens and the second lens in accordance with the following relation:

$$B = (L^{kl} + R^{kr})^{\frac{1}{kb}}$$

wherein,
B denotes the binocular visual performance,
L denotes the visual performance of one of the lenses,
R denotes the visual performance of the other lens, and
kl is a parameter having a value no less than 1.0, preferably in a range of about 1.4 to about 4,
kr is a parameter having a value no less than 1.0, preferably in a range of about 1.4 to about 4,
kb is a parameter having a value no less than 1.0, preferably in a range of about 1.4 to about 4, and
c) selecting the first and the second lenses so as to provide the patient with a stereo acuity better than about 120 arc seconds for any of near and distance vision.

24. A method of correcting vision, comprising the steps of:
a) providing a first lens for enhancing vision in one eye of a patient, and
b) providing a second lens for enhancing vision in the other eye of the patient,
wherein at least one of the first or the second lenses is a multifocal lens, and the first and the second lenses exhibit different focusing characteristics so as to provide the patient with a binocular visual performance in a selected range, the binocular visual performance being related to a visual performance of the first lens and the second lens in accordance with the following relation:

$$B = (L^{kl} + R^{kr})^{\frac{1}{kb}}$$

wherein,
B denotes the binocular visual performance,
L denotes the visual performance of one of the lenses,
R denotes the visual performance of the other lens, and
kl is a parameter having a value no less than 1.0, preferably in a range of about 1.4 to about 4,
kr is a parameter having a value no less than 1.0, preferably in a range of about 1.4 to about 4,
kb is a parameter having a value no less than 1.0, preferably in a range of about 1.4 to about 4, and
wherein the binocular visual performance is characterized by a stereo acuity and the stereo acuity is better than about 120 arc-second.

25. A lens kit for correcting a patient's vision, comprising
a) a first lens for use in one eye of the patient, and
b) a second lens for use in the other eye of the patient,
the first and the second lenses exhibiting different focusing characteristics so as to provide the patient with a binocular visual performance in a selected range,
wherein at least one of the first and the second lenses is a multifocal lens, and wherein the binocular visual performance is related to visual performances of the first and the second lenses in accordance with the following relation:

$$B = (L^{kl} + R^{kr})^{1/kb}$$

wherein,
B denotes the binocular visual performance,
L denotes the visual performance of one of the lenses,
R denotes the visual performance of the other lens, and
kl is a parameter having a value no less than 1.0, preferably in a range of about 1.4 to about 4,
kr is a parameter having a value no less than 1.0, preferably in a range of about 1.4 to about 4,
kb is a parameter having a value no less than 1.0, preferably in a range of about 1.4 to about 4, and
wherein the binocular visual performance is characterized by image contrast.

26. The method of claim 25, wherein kl, kr and kb are substantially equal to each other.

27. The kit of claim 25, wherein the binocular visual performance is characterized by visual acuity.

28. The kit of claim 25, wherein the binocular image contrast is in a range of about 10% to about 80% at a spatial frequency of about 15 cycles/degree.

29. The kit of claim 25, wherein the binocular image contrast is in a range of about 5% to about 60% at a spatial frequency of about 30 cycles/degree.

30. The kit of claim 27, wherein the binocular visual acuity is in a range of about 20/40 to about 20/10.

31. The kit of claim 25, wherein the multifocal lens exhibits a far-focus power in a range of about −15 D to about 40 D and an add power in a range of about 1 D to about 4 D.

32. The kit of claim 25, wherein the first and the second lenses comprise two multifocal lenses.

33. The kit of claim 32, wherein the first and the second lenses exhibit different add powers.

34. The kit of claim 33, wherein a difference between the add powers of the first and the second lenses is in a range of about 0.25 D to about 3 D.

35. The kit of claim 33, wherein a difference between the far focusing powers of the first and the second lenses is in a range of about 0.25 D to about 3 D.

36. The kit of claim 25, wherein the multifocal lens comprises at least one surface on which a plurality of diffractive zones separated by a plurality of steps are disposed, wherein the steps exhibit decreasing heights as a function of increasing distance from an optical axis of the multifocal lens.

37. The kit of claim 31, wherein the step heights associated with a diffractive zone is defined in accordance with the following relation:

$$\text{Step height} = \frac{\lambda}{a(n_2 - n_1)} f_{apodize}$$

wherein
  $\lambda$ denotes a design wavelength,
  a denotes a parameter for controlling diffraction efficiency associated with various orders,
  $n_2$ denotes the index of refraction of the optic,
  $n_1$ denotes the refractive index of a medium in which the lens is placed, and
  $f_{apodize}$ represents a scaling function whose value decreases as a function of increasing radial distance from the intersection of an optical axis with the surface of the lens.

38. The kit of claim 37, wherein the scaling function $f_{apodize}$ is defined in accordance with the following relation:

$$f_{apodize} = 1 - \left(\frac{r_i}{r_{out}}\right)^3$$

wherein
  $r_i$ denotes the radial distance of $i^{th}$ zone,
  $r_{out}$ denotes the outer radius of the last diffractive zone.

39. The kit of claim 31, wherein the multifocal lens comprises a plurality of diffractive zones disposed on a surface thereof, wherein a radial location of a zone boundary ($r_i$) is defined in accordance with the following relation:

$$r_i^2 = (2i+1)\lambda f$$

wherein
  i denotes the zone number (i=0 denotes the central zone),
  $r_i$ denotes the radial location of the $i^{th}$ zone,
  $\lambda$ denotes the design wavelength, and
  f denotes the focal length for an add power.

40. The kit of claim 25, wherein the multifocal lens comprises a plurality of diffractive zones disposed on a surface thereof, wherein a radial location of a zone boundary ($r_i$) is defined in accordance with the following relation $$r_i^2 = (2i+1)\lambda f + g(i)$$

wherein
  i denotes the zone number (i=0 denotes the central zone),
  $\lambda$ denotes the design wavelength,
  f denotes a focal length of the near focus, and
  g(i) denotes a non-constant function.

41. The kit of claim 40, wherein the function g(i) is defined in accordance with the following relation:

$$g(i) = (ai^2 + bi)f$$

wherein
  i denotes the zone number,
  a and b are two adjustable parameters, wherein a is in a range of about 0.1 $\lambda$ to about 0.3 $\lambda$ and b is in a range of about 1.5 $\lambda$ to about 2.5 $\lambda$, where $\lambda$, denotes a design wavelength.

42. The kit of claim 25, wherein one of the first and the second lenses is a multifocal lens and the other lens is a monofocal lens.

43. The kit of claim 42, wherein the monofocal lens exhibits a focusing power in a range of about −15 D to about 50 D.

44. The kit of claim 42, wherein the monofocal lens provides a focus intermediate of a near and a far focus of the multifocal lens.

45. The kit of claim 25, wherein the first and the second lenses comprise intraocular lenses.

* * * * *